United States Patent [19]
Ozawa

[11] Patent Number: 5,386,450
[45] Date of Patent: Jan. 31, 1995

[54] X-RAY PHOTOGRAPHING SYSTEM

[75] Inventor: Masahiro Ozawa, Tochigiken, Japan

[73] Assignee: Kabushiki Kaisha Toshiba, Kawasaki, Japan

[21] Appl. No.: 108,301

[22] Filed: Aug. 19, 1993

[30] Foreign Application Priority Data

Aug. 21, 1992 [JP] Japan .................. 4-222834

[51] Int. Cl.$^6$ .............................................. H05G 1/64
[52] U.S. Cl. .................. 378/98.2; 378/98.11; 378/62; 378/177
[58] Field of Search .............. 378/98.2, 98.11, 98.12, 378/177, 62

[56] References Cited

U.S. PATENT DOCUMENTS

5,111,492  5/1992  Klausz .................. 378/98.2

Primary Examiner—David P. Porta
Assistant Examiner—Don Wong
Attorney, Agent, or Firm—Oblon, Spivak, McClelland, Maier & Neustadt

[57] ABSTRACT

An X-ray photographing system obtains a temporal differential image from live images picked up with the position of a bed (5) on which a patient is laid being unchanged. The temporal differential image is stored in a third frame memory (12). According to the temporal differential image, a tracing unit (13) traces the flow at a contrast medium injected in the patient's blood vessels. A movement vector setting unit (14) sets movement vectors of the contrast medium. A movement decision unit (16) determines whether or not the bed must be moved according to a resultant vector obtained by adding the movement vectors together. The bed is moved according to the direction and size of a selected one of the movement vectors.

24 Claims, 9 Drawing Sheets

LIVE IMAGE

TEMPORAL DIFFERENTIAL IMAGE

BLOOD VESSEL A  BRANCH BLOOD VESSEL B

L1

L2

L12

MOVEMENT VECTOR T12

L3

L4

L34

MOVEMENT VECTOR T34

BED MOVING

L8

L9

L89

MOVEMENT VECTOR T89

L10

BED MOVING

X-RAY PHOTOGRAPHING SYSTEM

BACKGROUND OF THE INVENTION

Field of the Invention

The present invention relates to an X-ray photographing system having a DSA (digital subtraction angiography) function, and particularly, to an X-ray photographing system capable of correctly catching the flow of a contrast medium in blood vessels of a patient irrespective of artifacts.

Description of the Prior Art

An angiography is widely used to diagnose and treat a patient having trouble in circulatory organs. The angiography employs a catheter or a guide wire to inject a contrast medium into patient's blood vessels. The injected contrast medium is photographed by X-ray camera, and the picked up X-ray images are used to diagnose and treat the patient. When photographing a large area such as one of the legs of a patient, or when inserting a catheter up to a target part of a patient, it is necessary to move the X-ray camera or a bed on which the patient is laid, so that a contrast medium or the head of the catheter is always photographed or viewed. The X-ray camera or the bed may be manually moved by an operator. Such manual method is frequently employed when inserting a catheter into a patient. There is also an automatic method.

Figure 1:
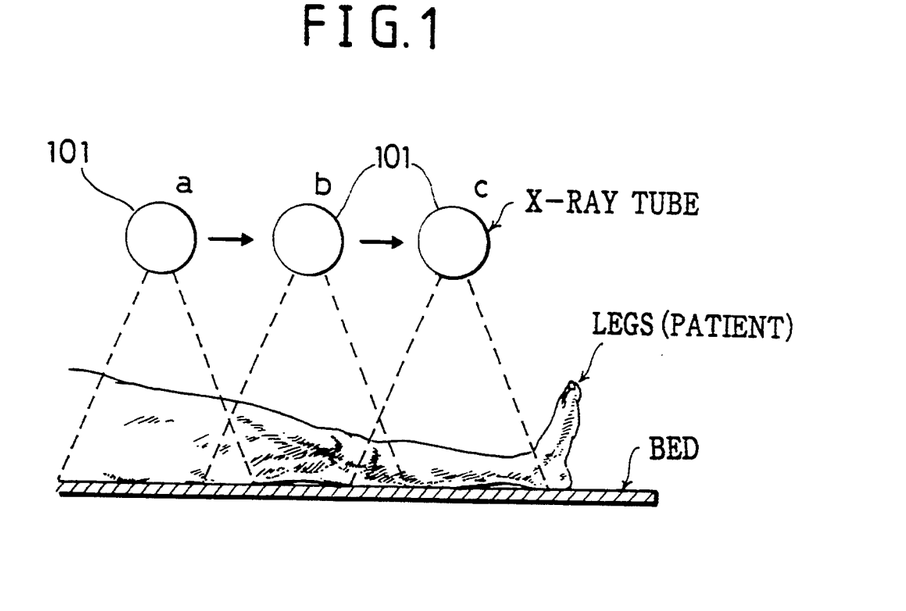
FIG. 1 explains movements of an X-ray tube of an X-ray photographing system according to a prior art.

FIG. 1 shows a conventional X-ray photographing system as an example of the automatic method. In the figure, the system picks up images of blood vessels of one of the legs of a patient. The system periodically moves an X-ray tube 101 in one direction from a position a to a position b, and from the position b to a position c.

Figure 2:
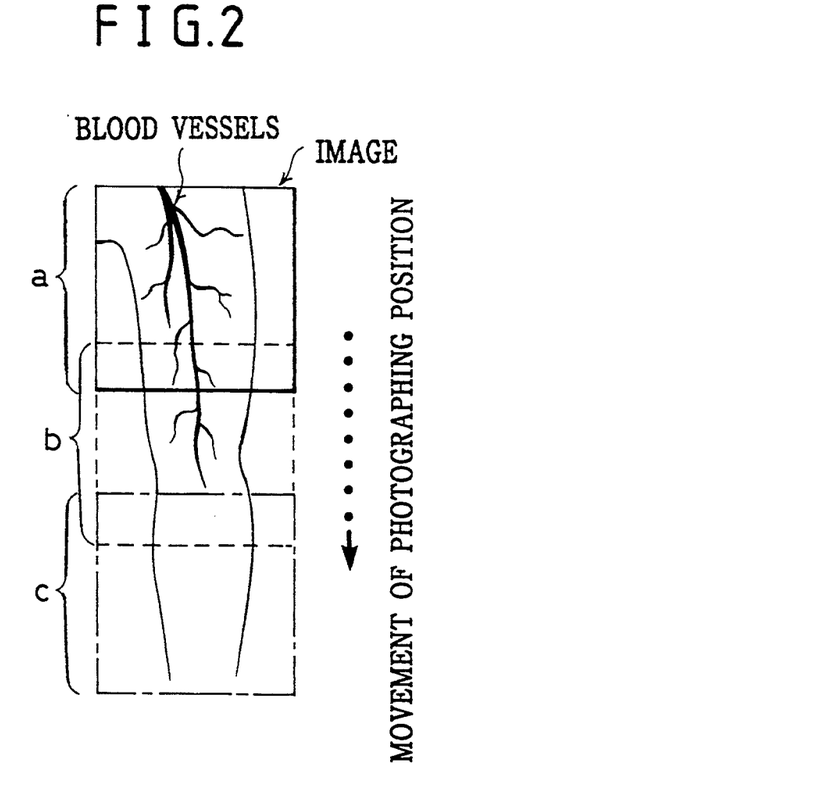
FIG. 2 explains changes in images provided by the system of FIG. 1.

FIG. 2 shows changes in images picked up by the system of FIG. 1.

This system automatically periodically moves the X-ray tube 101 with no regard to the flow of a contrast medium in the blood vessels. This system, therefore, will not always correctly provide images of a required region.

Figure 3:
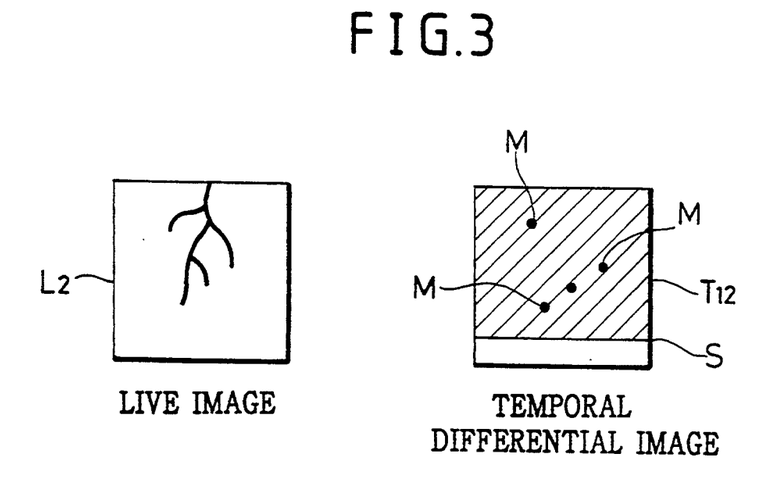
FIG. 3 shows images provided by an X-ray photographing system according to another prior art.
Figure 4:
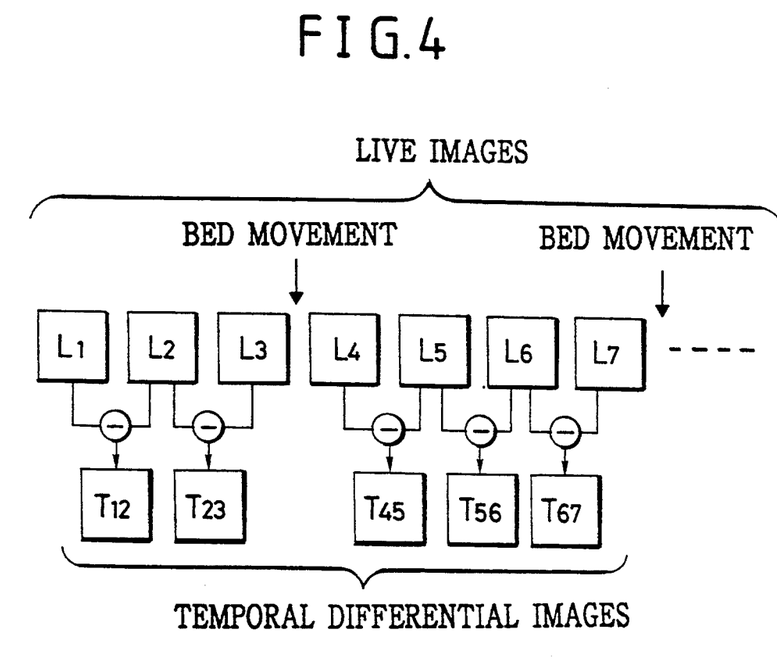
FIG. 4 explains temporal differential images and movements of a bed of the system of FIG. 3.

FIGS. 3 and 4 show images picked up by an X-ray photographing system that automatically moves a bed on which a patient is laid, to more correctly photograph a required region of the patient or the flow of a contrast medium in the patient.

The system photographs the patient at different time points without moving the bed at first, to provide live images L1, L2, and L3. These images are subtracted from one another to provide a temporal differential image T12 based on the images L1 and L2, a temporal differential image T23 based on the images L2 and L3, and so on. In each of the temporal differential images, points M having a highest concentration level are detected as leading ends of a contrast medium in blood vessels. If these points M are located below a predetermined line S, the bed with the patient is longitudinally moved for a predetermined distance. These processes are repeated according to successively obtained live images L4, L5, and so on, to thereby automatically move the bed with the patient. (This technique is disclosed in Japanese Laid-Open Patent Publication No. 3-53772.)

If an artifact (a virtual image) appears below the line S, the conventional X-ray photographing system may recognize the artifact as a point having the highest concentration, to improperly move the bed in response to the artifact before the actual leading ends of the contrast medium reach the line S. If the bed is improperly moved, the patient must be again photographed to elongate an inspection time and increase the quantity of X rays to which the patient is exposed.

Moreover, images of required regions may become out of sight because the bed is moved only longitudinally according to the conventional systems.

SUMMARY OF THE INVENTION

An object of tile present invention is to provide an X-ray photographing system that is capable of correctly functioning even if artifacts occur, automatically moving a bed on which a patient is laid according to the flow of a contrast medium injected in the patient's blood vessels or the movement of a catheter inserted in the blood vessels, and correctly photographing required regions of the patient.

In order to accomplish the object, a first aspect of the present invention provides an X-ray photographing system for emitting X rays toward a patient injected with a contrast medium, moving a bed on which the patient is laid according to the flow of the contrast medium, and providing images of a wide area of the patient's blood vessels.

The system employs a time difference unit for providing a temporal differential image based on live images picked up at the same bed position; a tracing unit for tracing trace points each having a maximum image concentration level above a predetermined level according to the temporal differential image; a movement vector setting unit for setting a movement vector for each of the trace points; a movement decision unit for selecting the largest one of the movement vectors and determining whether or not the selected vector extends beyond a zone defined around the start of the corresponding trace point; a movement calculation unit for calculating bed movements according to the selected vector when the movement decision unit determines that the selected vector extends beyond the zone; and a driving controller for driving the bed according to the calculated movements.

A second aspect of the present invention provides an X-ray photographing system for emitting X rays toward a patient injected with a contrast medium, moving a bed on which the patient is laid according to the flow of the contrast medium, and providing images of a wide area of blood vessels of the patient.

The system has a time difference unit for providing temporal differential image based on live images picked up at the same bed position; a tracing unit for tracing trace points each having a maximum image concentration level above a predetermined level according to the temporal differential image; a movement vector setting unit for setting a movement vector for each of the trace points; a vector adder for adding the movement vectors together to provide a resultant vector; a movement decision unit for selecting one of the movement vectors nearest to the resultant vector and determining whether or not the selected vector extends beyond a zone defined around the start of the corresponding trace point; a movement calculation unit for calculating bed movements according to the selected vector when the movement decision unit determines that the selected vector extends beyond the zone; and a driving controller for driving the bed according to the calculated movements.

According to the first and second aspects, points corresponding to ends of blood vessels may be traced according to live images without providing temporal differential images. The system may have a unit for adjusting the size of the zone defined around the start of the trace point. The bed and X-ray emitting unit may be moved relative to each other. It is possible to move the X-ray emitting unit instead of the bed.

A third aspect of the present invention provides an X-ray photographing system for emitting X rays toward a patient inserted with a catheter, moving a bed on which the patient is laid according to the movement of the catheter, and providing images of a wide area of blood vessels of the patient necessary for a catheter inspection.

The system has a time difference unit for providing a temporal differential image based on live images picked up at the same bed position; a tracing unit for tracing a trace point corresponding to the head of the catheter according to the temporal differential image; a movement vector setting unit for setting a movement vector for the trace point; a movement decision unit for determining whether or not the movement vector extends beyond a zone defined around the start of the trace point; a movement calculation unit for calculating bed movements according to the movement vector when the movement decision unit determines that the movement vector extends beyond the zone; and a driving controller for driving the bed according to the calculated movements.

This system may have a unit for detecting that the head of the catheter is moving backward according to the temporal differential image, recognizing according to the backward movement that the head of the catheter is slightly moving back and forth, and expanding the size of the zone defined around the start of the trace point. The system may have a unit for optionally adjusting the size of the zone defined around the start of the trace point. The bed and X-ray emitting unit may be moved relative to each other. It is possible to move the X-ray emitting unit instead of the bed.

in this way, the X-ray photographing system according to the first or the second aspect of the present invention traces the flow of a contrast medium according to temporal differential images and moves a bed according to movement vectors set according to results of the tracing. The X-ray photographing system according to the third aspect of the present invention traces the head of a catheter according to temporal differential images and moves a bed according to movement vectors set according to results of the tracing. Even if an artifact occurs at a position irrelevant to the flow of the contrast medium or the movement of the catheter in blood vessels, the systems according to the present invention will not erroneously act due to the artifact. The present invention adjusts the size of a reference zone defined around a tracing start point, to adjust the frequency of movements of a bed per unit time.

If the system according to the third aspect of the present invention is provided with the unit for expanding the size of a zone defined around the start of a trace point, the zone may be expanded to cover an area in which the head of a catheter may slightly move back and forth. Then, the bed will not be moved back and forth even if the head of the catheter is slightly moved back and forth to enter a branch blood vessel. This results in preventing useless movements of the bed and reducing fatigue of a patient on the bed.

These and other objects, features and advantages of the present invention will be more apparent from the following detailed description of preferred embodiments in conjunction with the accompanying drawings.

DETAILED DESCRIPTION OF THE EMBODIMENTS

The embodiments of the present invention will be explained with reference to the drawings.

Figure 5:
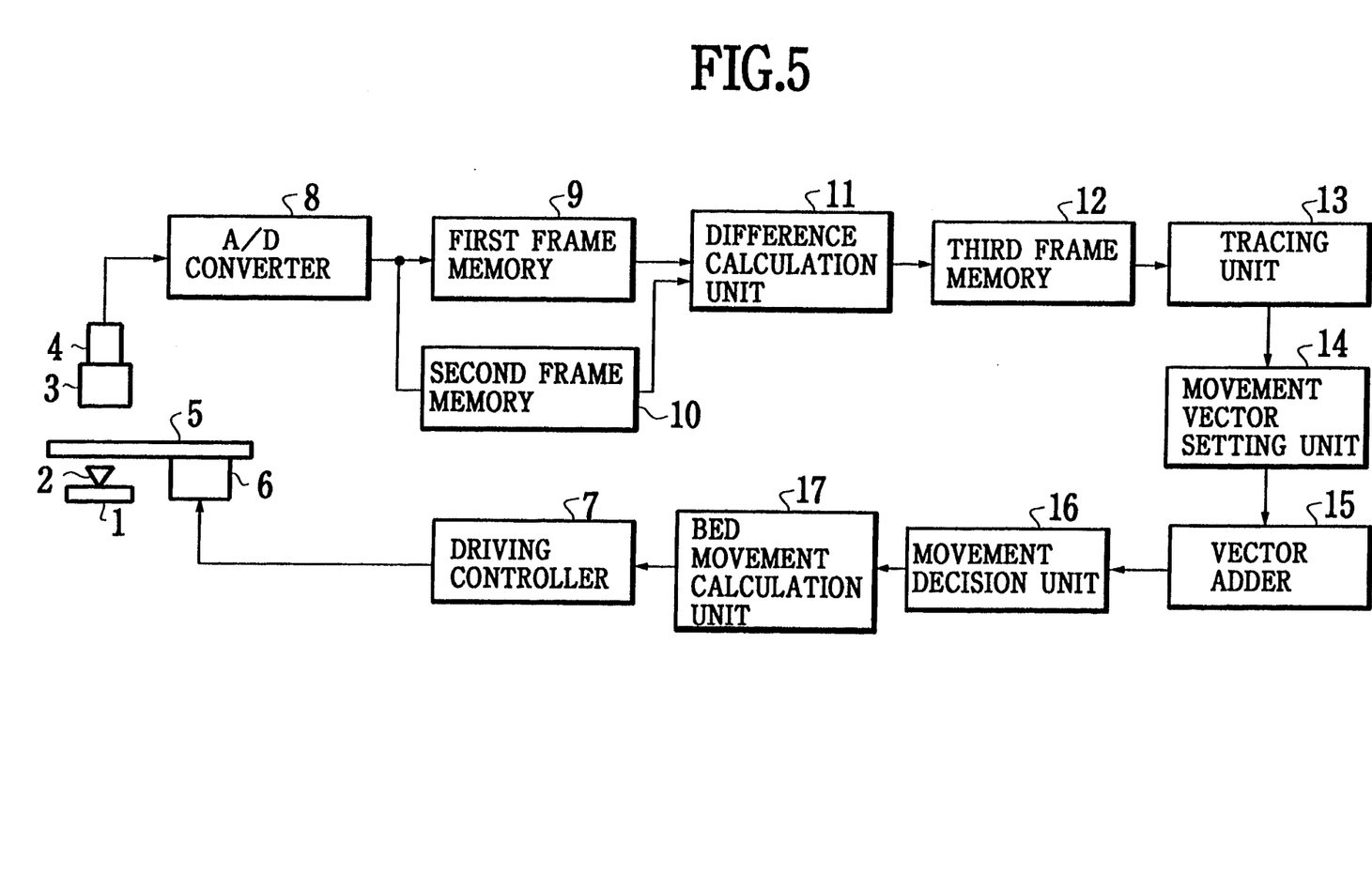
FIG. 5 is a block diagram showing essential parts of an X-ray photographing system according to a first embodiment of the present invention.

FIG. 5 is a block diagram showing essential parts of an X-ray photographing system according to the first embodiment of the present invention.

The system has an X-ray tube 1 for emitting X rays toward a patient, an X-ray diaphragm 2 for defining an area to irradiate with the X rays, an image intensifier 3 for converting X-ray image signals into optional image signals, a television camera 4 for converting the optical image signals into video image signals, a bed 5 on which the patient is laid, a bed driving unit 6 for longitudinally and laterally moving the bed 5, a driving controller 7 for providing the bed driving unit 6 with driving signals, an A/D converter 8 for converting the video image signals into digital signals, first and second frame memories 9 and 10 for storing live images, a difference calculation unit 11 for providing differences between the live images, a third frame memory 12 for storing a temporal differential image based on the differences, a tracing unit 13 for tracing the flow of a contrast medium in the patient, a movement vector setting unit 14 for setting a movement vector for each trace point, a vector adder 15 for adding the movement vectors together to provide a resultant vector, a movement decision unit 16 for determining whether or not the bed must be moved, and a bed movement calculation unit 17 for calculating the direction and distance of a movement of the bed.

Steps of photographing patient's blood vessels and moving the bed 5 will be explained with reference to FIGS. 5 and 6.

A patient is laid on the bed 5. A contrast medium is injected into a target part of tile patient. X rays are emitted toward the part, and an X-ray angiography image is picked up by the television camera 4 through the image intensifier 3. The image is stored as a live image L1 in the first frame memory 9 through the A/D converter 8. Another image is picked up at the same bed position and is stored as a live image L2 in the second frame memory 10. Thereafter, still another image is picked up at the same bed position and is stored as a live image L3 in the first frame memory 9. In this way, images are successively picked up and alternately stored in the first and second frame memories 9 and 10.

The difference calculation unit 11 subtracts the live image (for example, L1 or L3) stored in the first frame memory 9 from the live image (for example, L2) stored in the second frame memory, to provide a temporal differential image (for example, T12 or T23). The temporal differential image is stored in the third frame memory 12.

The tracing unit 13 traces a contrast medium in blood vessels on the temporal differential image provided by the third image frame 12, according to an algorithm called double-square-box region-of-search proposed by University of Chicago.

Figure 7A:
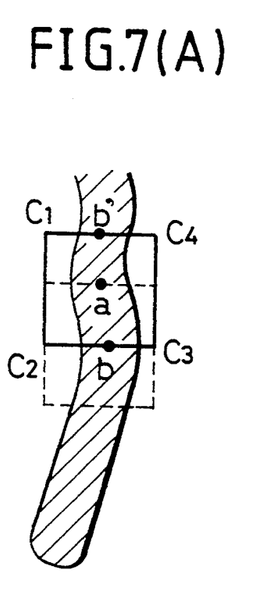
FIG. 7A and 7B explain a tracing method employed by the X-ray photographing system.
Figure 7B:
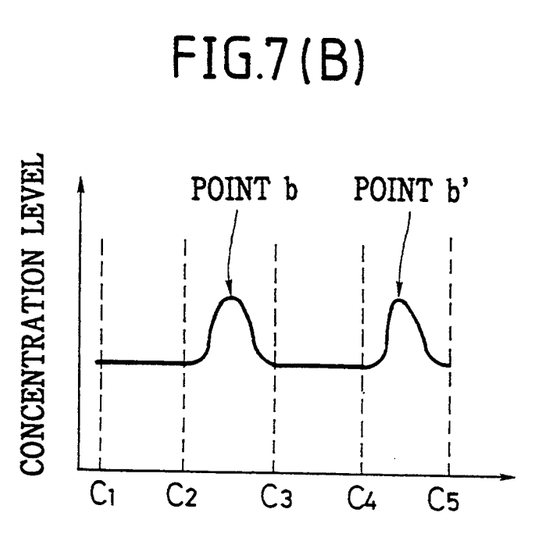

This algorithm employs the following steps:

(1) As shown in FIG. 7(a), a square having corners c1, c2, c3, and c4 is defined around a tracing start point a. The length of a side of the square is twice the diameter of a blood vessel at the point a.

(2) As shown in FIG. 7(b), a graph of image density levels at the sides of the square is prepared, and according to the graph, an image concentration distribution is found.

(3) A point b having a maximum concentration level above a predetermined level is selected according to the image concentration distribution, and the point b is set as the center of the blood vessel to be traced. If the blood vessel is curved more than 25 degrees, the sides of the square may be shortened to form a square of smaller size. A previously traced point b' will not be selected.

(4) The point b is set as a new tracing start point a, and the processes are repeated from the first step.

These four steps are repeated to trace the contrast medium injected in the blood vessels of the patient.

If no point having a concentration level above the predetermined level is detected other than the point b' in the third step, the tracing process ends. If there are a plurality of points b, each point will be traced.

The tracing unit 13 traces N leading ends of the contrast medium in blood vessels. The movement vector setting unit 14 sets N movement vectors V1 to Vn for the N leading ends of the contrast medium starting from a trace point P, as shown in FIG. 6. The vector adder 15 adds the movement vectors together to provide a resultant vector Va.

The movement decision unit 16 selects one of the movement vectors whose leading end is closest to the leading end of the resultant vector Va and determines whether or not the selected vector extends beyond a semicircular zone E (a hatched zone in FIG. 6) having a radius of 1 around the starting point P.

If the selected vector is within the semicircular zone E, the bed 5 will not be moved, and live images are successively alternately stored in the first and second frame memories 9 and 10, to repeat the process of obtaining another temporal differential image and the processes onward. The tracing is continued from the leading end of each movement vector.

If the selected vector extends beyond the semicircular zone E, the bed movement calculation unit 17 calculates the distance and direction of a movement of the bed 5, according to the selected vector.

Figure 6:
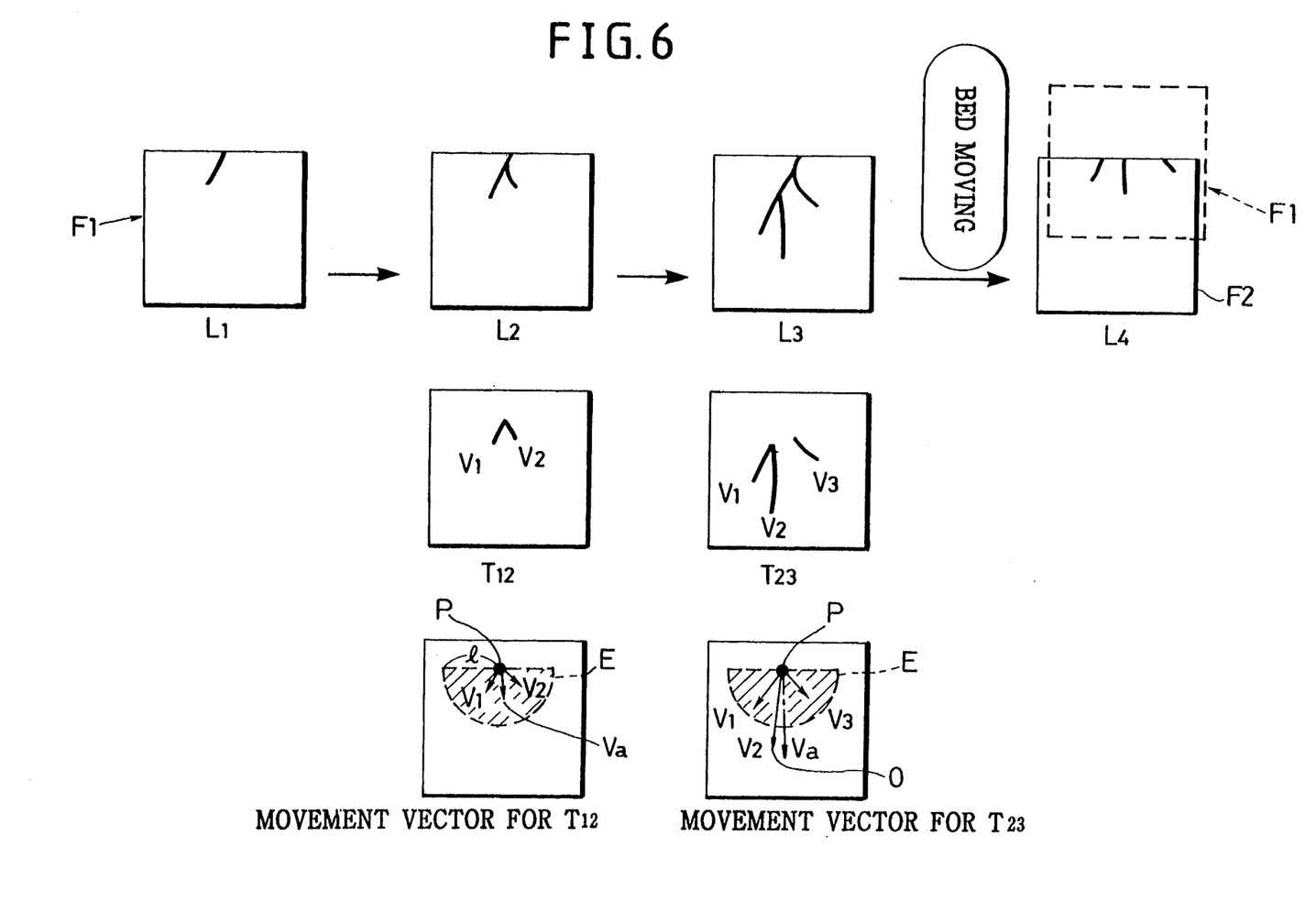
FIG. 6 explains relationships between live images and bed movements according to the embodiment of FIG. 5.

In the temporal differential image T12 of FIG. 6, a movement vector V1 adjacent to a resultant vector Va is within the semicircular zone E, so that the bed 5 will not be moved. In the temporal differential image T23, a movement vector V2 adjacent to a resultant vector Va extends beyond the semicircular zone E, so that the bed 5 will be moved.

To move the bed 5, the driving controller 7 drives the bed 5 according to the distance and direction calculated by the bed movement calculation unit 17. As a result, a photographing area is moved from F1 to F2. Then, live images are again collected, and the processes for moving the bed 5 are repeated.

After the bed 5 is moved, an end 0 of the selected vector is set as a new tracing start point to trace the contrast medium in the blood vessels.

The system program that controls the movement of the bed 5 may be programmed to optionally adjust the radius the semicircular zone E used to determine whether or not the bed 5 must be moved. To continuously move the bed 5, the radius may be shortened.

The movement decision unit 16 of the above embodiment selects a movement vector in the vicinity of a resultant vector and determines whether or not the selected vector extends beyond a semicircular zone E having a radius of 1 around the original point of the vector. The present invention is not limited to this. For example, a movement vector computation unit (not shown) is employed to set N movement vectors Vi having a tracing start point P as an origin, for N pieces of contrast medium leading ends provided by the tracing unit 13. The movement decision unit 16 then selects a maximum one of the movement vectors and determines whether or not the selected vector extends beyond the semicircular zone E of radius 1.

According to the first embodiment, the difference calculation unit 11 provides a temporal differential image such as T12 or T23 according to which the ends of blood vessels are traced. Instead, the ends of blood vessels may be traced according to live images without providing the temporal differential images.

Figure 8:
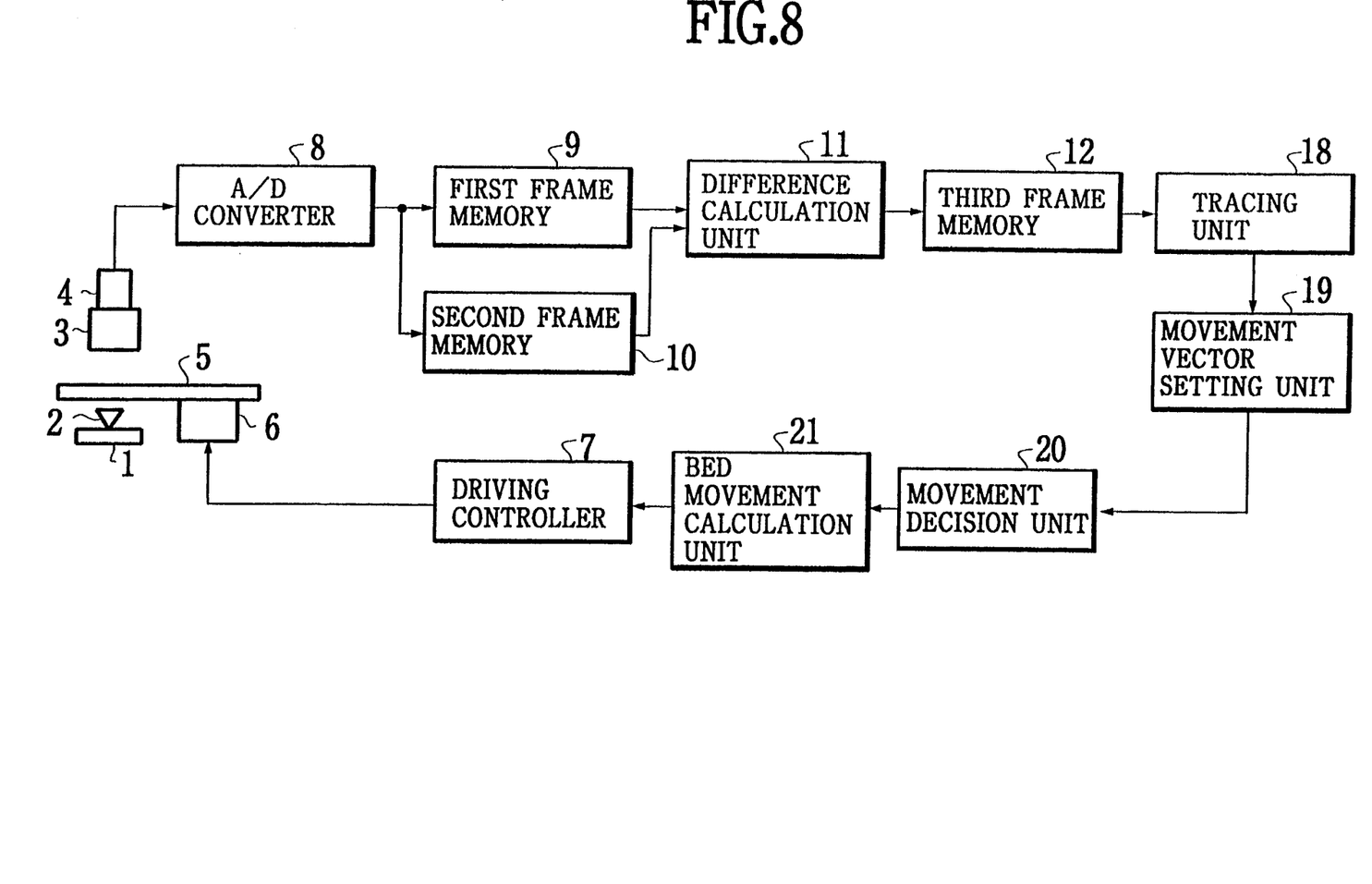
FIG. 8 is a block diagram showing essential parts of an X-ray photographing system according to a second embodiment of the present invention.

An X-ray photographing system according to a second embodiment of the present invention will be explained with reference to FIG. 8.

Similar to the first embodiment, the system of the second embodiment has an X-ray tube 1, an X-ray diaphragm 2, an image intensifier 3, a television camera 4, a bed 5 on which a patient is laid, a bed driving unit 6, a driving controller 7, an A/D converter 8, first and second frame memories 9 and 10, a difference calculation unit 11, and a third frame memory 12. The system further has a tracing unit 18 for tracing a trace point corresponding to the head of a catheter inserted in the patient, a movement vector setting unit 19 for setting a movement vector for the trace point, a movement decision unit 20 for determining whether or not the movement vector is beyond a predetermined level, and bed movement calculation unit 21 for calculating the distance and direction of a movement of the bed 5 according to the movement vector when the movement decision unit 20 determines that the movement vector is beyond the predetermined level.

Steps of moving the bed 5 in carrying out a catheter inspection will be explained.

A patient is laid on the bed 5. A contrast medium is injected in a target part of the patient. The part is irradiated with X rays. The television camera 4 picks up an X-ray image of the part through the image intensifier 3. The A/D converter 8 converts the X-ray image into a live image, and the first frame memory 9 stores the live image. Similarly, the second frame memory 10 stores another live image. In this way, the first and second frame memories 9 and 10 alternately store live images.

Figure 9:
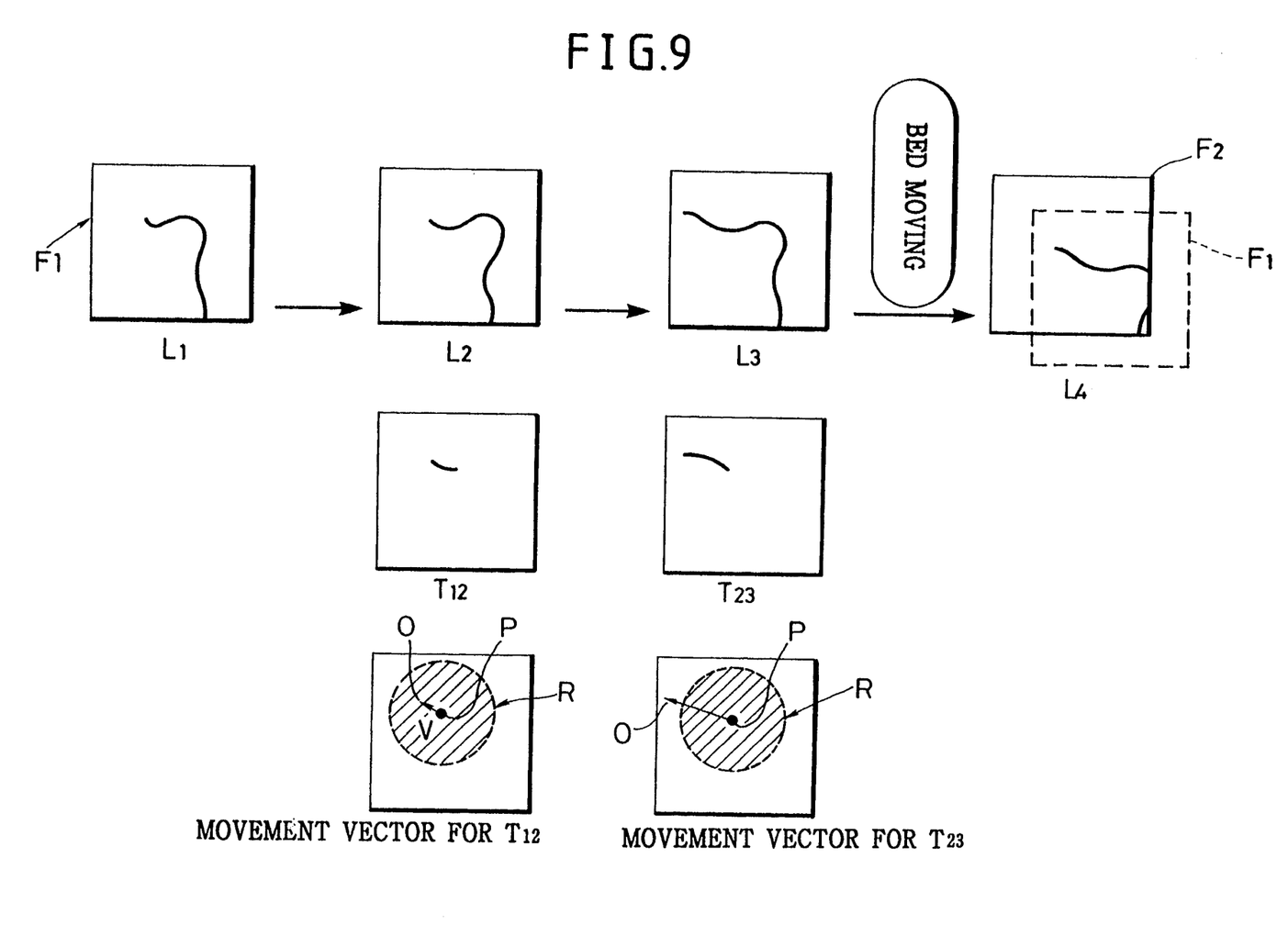
FIG. 9 explains relationships between temporal differential images and bed movements according to the second embodiment of the present invention.

In FIG. 9, the difference calculation unit 11 calculates temporal differences between the two live images (for example, between L1 and L2, or between L2 and L3) stored in the first and second frame memories 9 and 10 and provides a temporal differential image (for example, T12 T23). The temporal differential image is stored in the third frame memory 12.

According to the same tracing method as of the first embodiment, the tracing unit 18 traces the head of the catheter according to the temporal differential image. The movement vector setting unit 19 sets a movement vector V extending from a trace starting point P to the present position of the head 0 of the catheter.

The movement decision unit 20 determines whether or not the movement vector V extends beyond a circular zone R (a hatched zone in FIG. 9) having a radius of 1 around the trace starting point P. If the movement vector V is within the circular zone R, the bed 5 is not moved, a next live image is stored in one of the first and second frame memories 9 and 10, and the steps of providing a temporal differential image are repeated.

If the movement vector V extends beyond the circular zone R, the bed movement calculation unit 21 calculates the distance and direction of a movement of the bed 5 according to the movement vector V. The driving controller 7 moves the bed 5 according to the calculated distance and direction. As a result, a photographing area is moved from F1 to F2, a live image L4 is picked up, and the steps of moving the bed 5 are repeated.

In this way, this embodiment correctly moves the bed 5 according to the movement of the head of the catheter.

The system program that controls the movement of the bed 5 may be programmed to optionally adjust the radius of the circular zone R used to determine whether or not the bed 5 must be moved. To continuously move the bed 5, the radius may be shortened.

Figure 10:
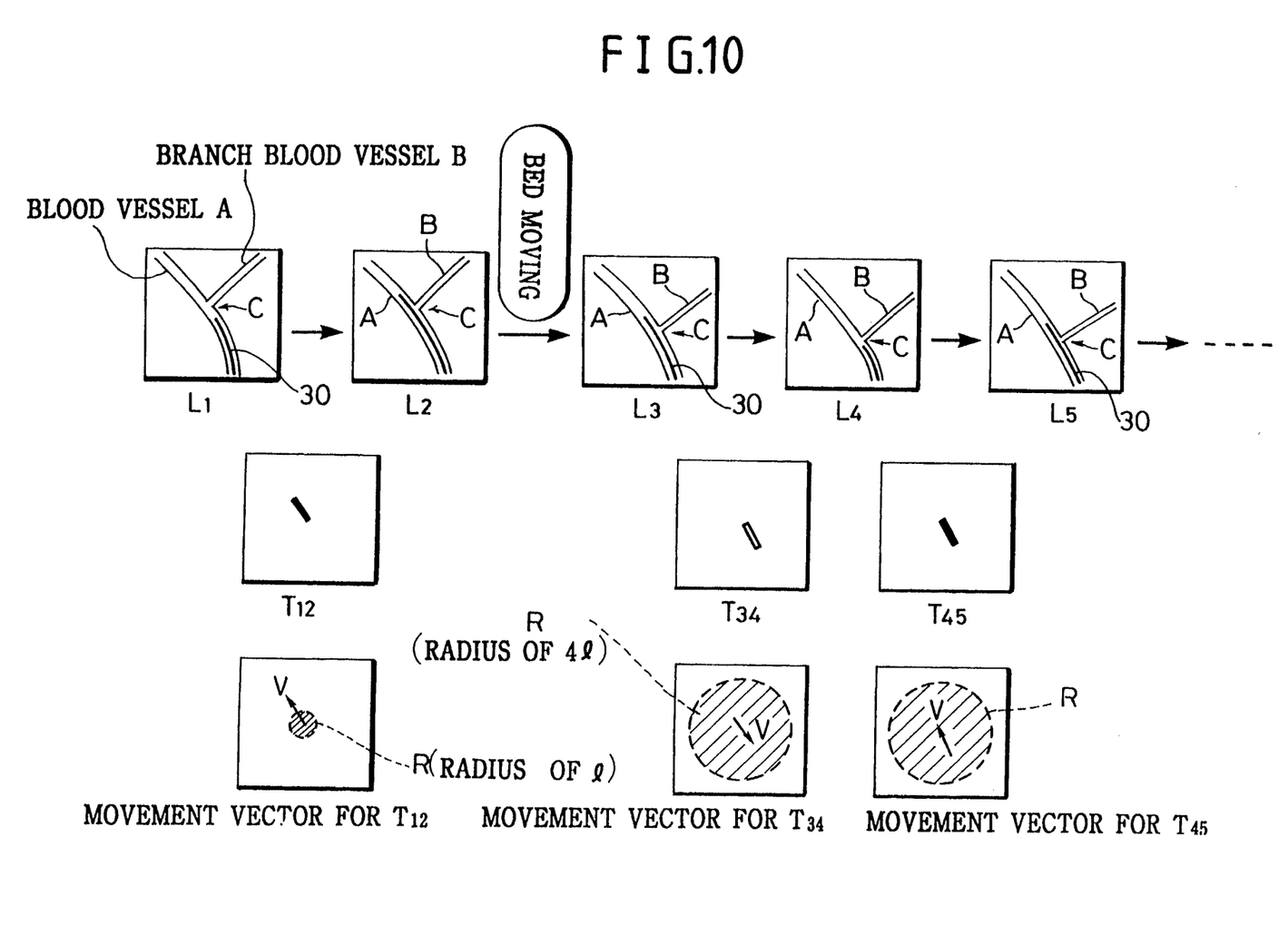
FIG. 10 shows a first modification of the second embodiment of the present invention.

FIG. 10 shows a catheter 30 to be guided from a blood vessel A into a branch blood vessel B according to the X-ray photographing system of the second embodiment. In this case, the head of the catheter 30 is usually moved back and forth at a branching point C. This results in uncomfortably moving the bed 5 back and forth and providing blood vessel images that are hard to see. To prevent this, the second embodiment provides two modifications that enlarge the size of the circular zone R used to determine whether or not the bed 5 must be moved.

The first modification will be explained with reference to FIG. 10. This modification enlarges the circular zone R upon detecting that the catheter 30 is moving back and forth at the branching point C in guiding the catheter from the blood vessel A into the branch blood vessel B.

In the figure, L1 to L5 are live image, T12 to T45 are temporal differential images formed from the live images (for example, the temporal differential image T12 is formed from the live images L1 and L2), V is a movement vector set in each of the temporal differential images, and R is a circular zone used to determine whether or not the bed 5 must be moved. Each of the live images shows the running states of the blood vessels A and B.

The steps of preventing slight movements of the bed 5 according to the first modification will be explained.

(1) When guiding the catheter 30 from the blood vessel A into the branch B, the head of the catheter 30 is moved back and forth in the blood vessel A around the branching point C. When the catheter 30 is moved backward, the temporal differential image T34 formed from the live images L3 and L4 becomes white, unlike the temporal differential image T12 that is black. This phenomenon is used to detect the back-and-forth movements of the catheter 30. The movement decision unit 20 of FIG. 8 is used to detect such back-and-forth movements.

(2) When the back-and-forth movements are detected, the radius of the circular zone R used to determine whether or not the bed 5 must be moved is enlarged four times as large as the original radius.

(3) Once the circular zone R is enlarged, a movement vector V corresponding to the slight back-and-forth movements of the catheter 30 becomes within the circular zone R. Accordingly, the bed 5 will not be moved in response to the back-and-forth movements. When the movement vector V extends beyond the enlarged circular zone R, the radius of the circular zone R is returned to the original one, to continue the tracing operation.

Figure 11:
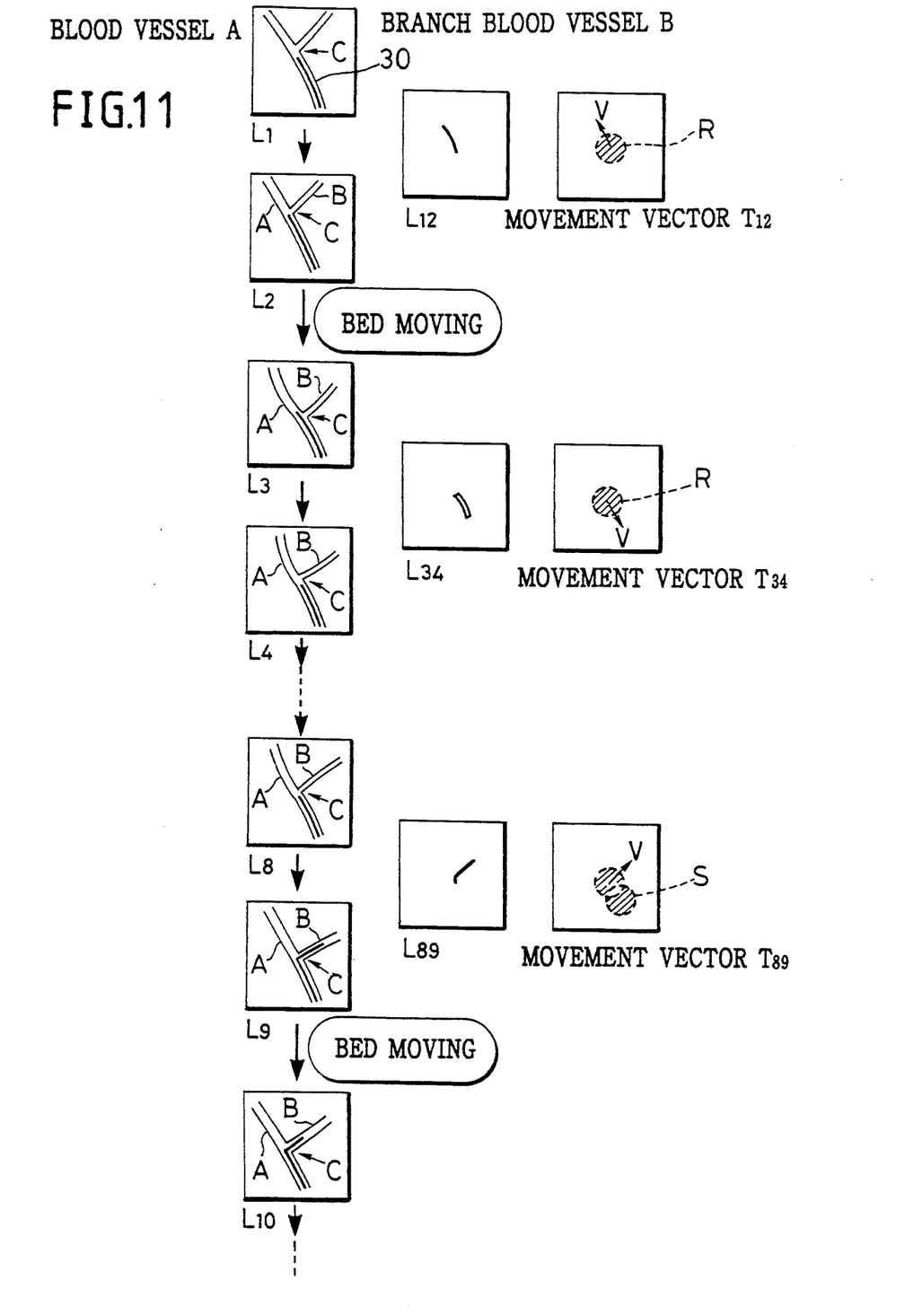
FIG. 11 shows a second modification of the second embodiment of the present invention.

FIG. 11 shows the second modification of the second embodiment, applicable when guiding the catheter 30 from the blood vessel A into the branch blood vessel B at the branching point C. This modification changes the circular zone R into a belt zone S extending in the direction of the back-and-forth movements of the catheter 30 when the back-and-forth movements are detected.

In the figure, L1 to L10 are live images, T12 to T89 are temporal differential images formed from the live images (for example, the temporal differential image T12 is formed from the live images L1 and L2), V is a movement vector set in each of the temporal differential images, and R is a circular zone used to determine whether or not the bed 5 must be moved. Each of the live images shows the running states of the blood vessels A and B.

The steps of preventing slight movements of the bed 5 according to the second modification will be explained.

(1) When guiding the catheter 30 from the blood vessel A into the branch B, the head of the catheter 30 is moved back and forth around the branching point C. When the catheter 30 is moved backward, the temporal differential image T34 formed from the live images L3 and L4 becomes white, unlike the temporal differential image T12 that is black. This phenomenon is used to detect such back-and-forth movements of the catheter 30.

(2) When the back-and-forth movements are detected, the circular zone R used to determine whether or not the bed 5 must be moved is changed into a belt zone S that is defined by circles drawn around the head of the catheter 30 that is moving backward. The belt zone S extends in the direction of the back-and-forth movements.

(3) Once the belt zone S is defined, a movement vector V corresponding to the slight back-and-forth movements of the catheter 30 becomes within the belt zone S.

Accordingly, the bed 5 will not be moved in response to the back-and-forth movements. When the movement vector V extends beyond the belt zone S, the belt zone S is returned to the original circular zone R, to continue the tracing operation.

The above embodiments move the bed 5. This does not limit the present invention. The present invention is also applicable for moving the bed 5 and X-ray tube 1 relative to each other.

In summary, the present invention provides an X-ray photographing system that moves an X-ray tube or a bed on which a patient is laid according to the flow of a contrast medium or the movement of a catheter in the patient. Even if an artifact occurs at a position irrelevant to the position of the contrast medium or the catheter, the present invention will never erroneously move the bed or the X-ray tube. The present invention automatically moves the bed or the X-ray tube according to the flow of the contrast medium or the movement of the catheter, to reduce load on an operator and decrease the quantity of X rays to which the patient is exposed. The flow of the contrast medium and the movement of the head of the catheter can be traced on a display to automatically correctly move the bed or the X-ray tube, and the flow of the contrast medium and the movement of the head of the catheter will not escape from the screen of the display or from a photographing zone.

Various modifications will become possible for those skilled in the art after receiving the teachings of the present disclosure without departing from the scope thereof.

What is claimed is:

1. An X-ray photographing system for emitting X rays from X-ray emitting means toward a patient injected with a contrast medium, moving the patient and X-ray emitting means relative to each other along the flow of the contrast medium, and providing images of a wide area of blood vessels of the patient, comprising:
    tracing means for tracing trace points each corresponding to an end of an objective blood vessel according to image concentration data of images picked up at a predetermined relative position of the patient and X-ray emitting means;
    movement vector setting means for setting a movement vector for each of the trace points;
    movement decision means for selecting the largest one of the movement vectors and determining whether or not the selected vector extends beyond a zone defined around the start of the corresponding trace point;
    movement calculation means for calculating relative movements of the patient and X-ray emitting means according to the selected vector when said movement decision means determines that the selected vector extends beyond the zone; and
    driving control means for relatively driving the patient and X-ray emitting means according to the calculated relative movements.

2. The X-ray photographing system according to claim 1, further comprising:
    means for adjusting the size of the zone defined around the start of the trace point.

3. An X-ray photographing system for emitting X rays from X-ray emitting means toward a patient injected with a contrast medium, moving the patient and X-ray emitting means relative to each other along the flow of the contrast medium, and providing images of a wide area of blood vessels of the patient, comprising:
    time difference means for providing a temporal differential image based on live images picked up at the same relative position of the patient and X-ray emitting means;
    tracing means for tracing trace points each corresponding to an end of an objective blood vessel according to image concentration data of the temporal differential image;
    movement vector setting means for setting a movement vector for each of the trace points;
    movement decision means for selecting the largest one of the movement vectors and determining whether or not the selected vector extends beyond a zone defined around the starting point of the corresponding trace point;
    movement calculation means for calculating relative movements of the patient and X-ray emitting means according to the selected vector when said movement decision means determines that the selected vector extends beyond the zone; and
    driving control means for relatively driving the patient and X-ray emitting means according to the calculated relative movements.

4. The X-ray photographing system according to claim 3, further comprising:
    means for adjusting the size of the zone defined around the start of the trace point.

5. An X-ray photographing system for emitting X rays from X-ray emitting means toward a patient injected with a contrast medium, moving the patient and X-ray emitting means relative to each other along the flow of the contrast medium, and providing images of a wide area of blood vessels of the patient, comprising:
    tracing means for tracing trace points each corresponding to an end of an objective blood vessel according to image concentration data of images picked up at a predetermined relative position of the patient and X-ray emitting means;
    movement vector setting means for setting a movement, vector for each of the trace points;
    vector adding means for adding the movement vectors together to provide a resultant vector;
    movement decision means for selecting one of the movement vectors nearest to the resultant vector and determining whether or not the selected vector extends beyond a zone defined around the start of the corresponding trace point;
    movement calculation means for calculating relative movements of the patient and X-ray emitting means according to the selected vector when said movement decision means determines that the selected vector extends beyond the zone; and
    driving control means for relatively driving the patient and X-ray emitting means according to the calculated relative movements.

6. The X-ray photographing system according to claim 5, further comprising:
    means for adjusting the size of the zone defined around the start of the trace point.

7. An X-ray photographing system for emitting X rays from X-ray emitting means toward a patient injected with a contrast medium, moving the patient and X-ray emltting means relative to each other along the flow of the contrast medium, and providing images of a wide area of blood vessels of the patient, comprising:
    time difference means for providing a temporal differential image based on live images picked up at the same relative position of the patient and X-ray emitting means;

tracing means for tracing trace points each corresponding to an end of an objective blood vessel according to image concentration data of the temporal differential image;

movement vector setting means for setting a movement vector for each of the trace points;

vector adding means for adding the movement vectors together to provide a resultant vector;

movement decision means for selecting one of the movement vectors nearest to the resultant vector and determining whether or not the selected vector extends beyond a zone defined around the start of the corresponding trace point;

movement calculation means for calculating relative movements of the patient and X-ray emitting means according to the selected vector when said movement decision means determines that the selected vector extends beyond the zone; and driving control means for relatively driving the patient and X-ray emitting means according to the calculated relative movements.

8. The X-ray photographing system according to claim 7, further comprising:

means for adjusting the size of the zone defined around the start of the trace point.

9. An X-ray photographing system for emitting X rays toward a patient injected with a contrast medium, moving a bed on which the patient is laid according to the flow of the contrast medium, and providing images of a wide area of blood vessels of the patient, comprising:

tracing means for tracing trace points each corresponding to an end of an objective blood vessel according to image concentration data of images picked up at a predetermined bed position;

movement vector setting means for setting a movement vector for each of the trace points;

movement decision means for selecting the largest one of the movement vectors and determining whether or not the selected vector extends beyond a zone defined around the starting point of the corresponding trace point;

movement calculation means for calculating bed movements according to the selected vector when said movement decision means determines that the selected vector extends beyond the zone; and driving control means for driving the bed according to the calculated movements.

10. The X-ray photographing system according to claim 9, further comprising:

means for adjusting the size of the zone defined around the start of the trace point.

11. An X-ray photographing system for emitting X rays toward a patient injected with a contrast medium, moving a bed on which the patient is laid according to the flow of the contrast medium, and providing images of a wide area of blood vessels of the patient, comprising:

time difference means for providing a temporal differential image based on live images picked up at the same bed position;

tracing means for tracing trace points each having a maximum image concentration level above a predetermined level according to the temporal differential image;

movement vector setting means for setting a movement vector for each of the trace points;

movement decision means for selecting the largest one of the movement vectors and determining whether or not the selected vector extends beyond a zone defined around the starting point of the corresponding trace point;

movement calculation means for calculating bed movements according to the selected vector when said movement decision unit determines that the selected vector extends beyond the zone; and driving control means for driving the bed according to the calculated movements.

12. The X-ray photographing system according to claim 11 further comprising:

means for adjusting the size of the zone defined around the start of the trace point.

13. An X-ray photographing system for emitting X rays toward a patient injected with a contrast medium, moving a bed on which the patient is laid according to the flow of the contrast medium, and providing images of a wide area of blood vessels of the patient, comprising:

tracing means for tracing trace points each corresponding to an end of an objective blood vessel according to image concentration data of images picked up at a predetermined bed position;

movement vector setting means for setting a movement vector for each of the trace points;

vector adding means for adding the movement vectors together to provide a resultant vector;

movement decision means for selecting one of the movement vectors nearest to the resultant vector and determining whether or not the selected vector extends beyond a zone defined around the start of the corresponding trace point;

movement calculation means for calculating bed movements according to the selected vector when said movement decision means determines that the selected vector extends beyond the zone; and driving control means for driving the bed according to the calculated movements.

14. The X-ray photographing system according to claim 13, further comprising:

means for adjusting the size of the zone defined around the start of the trace point.

15. An X-ray photographing system for emitting X rays toward a patient injected with a contrast medium, moving a bed on which the patient is laid according to the flow of the contrast medium, and providing images of a wide area of blood vessels of the patient, comprising:

time difference means for providing a temporal differential image based on live images picked up at the same bed position;

tracing means for tracing trace points each having a maximum image concentration level above a predetermined level according to the temporal differential image;

movement vector setting means for setting a movement: vector for each of the trace points;

vector adding means for adding the movement vectors together to provide a resultant vector;

movement decision means for selecting one of the movement vectors nearest to the resultant vector and determining whether or not the selected vector extends beyond a zone defined around the start of the corresponding trace point;

movement calculation means for calculating bed movements according to the selected vector when said movement decision means determines that the selected vector extends beyond the zone; and driving control means for driving the bed according to the calculated movements.

16. The X-ray photographing system according to claim 15, further comprising:

means for adjusting the size of the zone defined around the start of the trace point.

17. An X-ray photographing system for emitting X rays from X-ray emitting means toward a patient inserted with a catheter, moving the patient and X-ray emitting means relative to each other according to the insertion of the catheter, and providing images of blood vessels of the patient necessary for a catheter inspection, comprising:

time difference means for providing a temporal differential image based on live images picked up at a predetermined relative position of the patient and X-ray emitting means;

tracing means for tracing a trace point corresponding to the head of the catheter according to the temporal differential image;

movement vector setting means for setting a movement vector for the trace point;

movement decision means for determining whether or not the movement vector extends beyond a zone defined around the start of the trace point;

movement calculation means for calculating relative movements of the patient and X-ray emitting means according to the movement vector when said movement decision means determines that the movement vector extends beyond the zone; and driving control means for relatively driving the patient and X-ray emitting means according to the calculated relative movements.

18. The X-ray photographing system according to claim 17, further comprising:

means for detecting according to the temporal differential image that the head of the catheter is moving backward, recognizing according to the backward movement that the head of the catheter is slightly moving back and forth, and expanding the size of the zone defined around the start of the trace point.

19. The X-ray photographing system according to claim 17, further comprising:

means for adjusting the size of the zone defined around the start of the trace point.

20. The X-ray photographing system according to claim 19, further comprising:

means for detecting according to the temporal differential image that the head of the catheter is moving backward, recognizing according to the backward movement that the head of the catheter is slightly moving back and forth, and expanding the size of the zone defined around the start of the trace point.

21. An X-ray photographing system for emitting X rays toward a patient inserted with a catheter, moving a bed on which the patient is laid according to the movement of the catheter, and providing images of blood vessels of the patient necessary for a catheter inspection, comprising:

time difference means for providing a temporal differential image based on live images picked up at the same bed position;

tracing means for tracing a trace point corresponding to the head of the catheter according to the temporal differential image;

movement vector setting means for setting a movement vector for the trace point;

movement decision means for determining whether or not the movement vector extends beyond a zone defined around the start of the trace point;

movement calculation means for calculating bed movements according to the movement vector when said movement decision means determines that the movement vector extends beyond the zone; and driving control means for driving the bed according to the calculated movements.

22. The X-ray photographing system according to claim 21, further comprising:

means for detecting according to the temporal differential image that the head of the catheter is moving backward, recognizing according to the backward movement that the head of the catheter is slightly moving back and forth, and expanding the size of the zone defined around the start of the trace point.

23. The X-ray photographing system according to claim 21, further comprising:

means for adjusting the size of the zone defined around the start of the trace point.

24. The X-ray photographing system according to claim 23, further comprising:

means for detecting according to the temporal differential image that the head of the catheter is moving backward, recognizing according to the backward movement that the head of the catheter is slightly moving back and forth, and expanding the size of the zone defined around the start of the trace point.

* * * * *